United States Patent
Lerner

(10) Patent No.: US 8,285,489 B2
(45) Date of Patent: Oct. 9, 2012

(54) MULTI-STAGE, REGRESSION-BASED PCR ANALYSIS SYSTEM

(75) Inventor: Jeffrey Lerner, Oakland, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 444 days.

(21) Appl. No.: 12/556,416

(22) Filed: Sep. 9, 2009

(65) Prior Publication Data

US 2010/0070190 A1    Mar. 18, 2010

Related U.S. Application Data

(60) Provisional application No. 61/095,410, filed on Sep. 9, 2008.

(51) Int. Cl.
*G01N 33/48* (2006.01)
*G06F 11/30* (2006.01)
(52) U.S. Cl. ............ 702/19; 702/182; 702/189; 702/190
(58) Field of Classification Search ............... 702/19, 702/121–123, 181–190
See application file for complete search history.

(56) References Cited

U.S. PATENT DOCUMENTS

| | | | |
|---|---|---|---|
| 6,232,079 B1 | 5/2001 | Wittwer et al. | |
| 6,783,934 B1 | 8/2004 | McMillan et al. | |
| 6,911,327 B2 | 6/2005 | McMillan et al. | |
| 2006/0269947 A1* | 11/2006 | Lerner | ............. 435/6 |
| 2006/0271308 A1* | 11/2006 | Lerner | ............. 702/19 |

FOREIGN PATENT DOCUMENTS

| | | |
|---|---|---|
| EP | 1 335 028 | 8/2003 |
| WO | WO 03/067215 A | 8/2003 |

OTHER PUBLICATIONS

Livak, Kenneth et al., "Analysis of Relative Gene Expression Data Using Real-Time Quantitative PCR and the 2-ΔΔCT Method," *Elsevier Science*, Methods 25, pp. 402-408 (2001).
Dheda, Keertan, et al., "Validation of housekeeping genes for normalizing RNA expression in real-time PCR," *BioTechniques*, vol. 37, pp. 112-119, (Jul. 2004).
Extended European Search Report EP 06 75 9657, dated Aug. 6, 2008.
Tichopad, Ales et al.; "Improving quantitative real-time RT-PCR reproducibility by boosting primer-linked amplification efficiency"; 2002, *Biotechnology Letters*, vol. 24, pp. 2053-2056.
Office Action dated May 19, 2009 from U.S. Appl. No. 11/433,183; 6 pages.

(Continued)

*Primary Examiner* — Phuong Huynh
(74) *Attorney, Agent, or Firm* — David B. Raqczkowski; Kilpatrick Townsend & Stockton LLP

(57) ABSTRACT

Systems and methods are provided for analyzing data to determine properties of a PCR process or other process exhibiting amplification or growth. Data representing an amplification can be distinguished from data representing a jump or other error. A modified sigmoid function containing a drift term may be used in determining the properties. A multi-stage functional fit of the amplification data can provide increased accuracy and consistency of one or more of the properties. A baseline of the amplification data can be determined by analyzing an integrated area of a first derivative function of the data. A reference quantitation value can also be determined from locations of maxima of different derivative functions of the amplification data, e.g., a weighted average of the maxima locations for the second and third derivatives may be used.

27 Claims, 13 Drawing Sheets

OTHER PUBLICATIONS

Office Action dated Mar. 31, 2009 from U.S. Appl. No. 11/432,856; 6 pages.
Notice of Allowance dated Sep. 4, 2009 from U.S. Appl. No. 11/432,856; 6 pages.
Search/Examination Report dated Oct. 28, 2009 from International Application No. PCT/US09/56384, 10 pages.
Roche Molecular Biochemicals, "LightCycler Software, Version 3," Biochemica, 1999, pp. 16-18, No. 2.

* cited by examiner

US 8,285,489 B2

MULTI-STAGE, REGRESSION-BASED PCR ANALYSIS SYSTEM

CLAIM OF PRIORITY

The present application claims priority from and is a non-provisional application of U.S. Provisional Application No. 61/095,410, entitled "MULTI-STAGE, REGRESSION-BASED PCR ANALYSIS SYSTEM", filed Sep. 9, 2008, the entire contents of which are herein incorporated by reference for all purposes.

BACKGROUND

The present invention relates generally to data processing systems and methods that analyze data resulting from biological and/or chemical reactions exhibiting amplification, such as a polymerase chain reaction (PCR).

Many experimental processes exhibit amplification of a quantity. For example, in PCR, the quantity may correspond to the number of parts of a DNA strand that have been replicated, which dramatically increases during an amplification stage that is exhibited in an amplification region of a PCR data plot. PCR data is typically described by a region showing a linear drifting baseline, which is a precursor to exponential growth in the amplification region. As the consumables are exhausted, the curve turns over and asymptotes. Other experimental processes exhibiting amplification include bacterial growth processes.

The quantity of the experimental process is detected from an experimental device via a data signal. For example, the data can be collected by imaging different excitation wavelengths and emission wavelengths from one or more reactions occurring in respective wells or tubes. The data signal contains data points that are analyzed to determine information about the amplification. The collected data is then typically stored for future use.

One example of an analysis that might be conducted using PCR data is known as baselining. The baseline represents noise or instrument-specific levels in the data, not amplification. In order to better analyze the amplification region of the data, it is often desirable to remove the linear drifting baseline from the data signal. Such baselining can help to determine the level of actual amplification above the baseline. For certain types of analysis, this allows comparison between the amplification levels of different curves, since the baselines can vary on a per-curve basis. An example of baselining can be found in US Patent Publication 2006/0269947, incorporated by reference for all purposes.

Another analysis often conducted using PCR data is to calculate some quantification, in either absolute or relative terms, of a specific target molecule in the reaction. This can be accomplished by designating a target signal threshold that corresponds to a reference threshold. The number of cycles required to reach this target threshold is then referred to as the Ct value. Previous methods for determining the Ct value of a reaction are often limited, for example, by the accuracy of the modeling of the raw data or noise in the raw data.

Although methods exist for these and other types of analysis, data collected from amplification systems often includes significant noise and other variable aspects, which can hinder an efficient and accurate determination of characteristics of a reaction. Accordingly, new methods for analyzing amplification curves are desired.

BRIEF SUMMARY

Embodiments provide systems, methods, and apparatus for analyzing data to determine properties of a PCR process or other process exhibiting amplification. In one embodiment, a multiple-stage functional fit can be used to increase an accuracy of the determined properties. In one aspect, the properties include a baseline, a reference quantitation value (e.g. a Ct value) of the amplification process, whether amplification exists, and an efficiency of the amplification process.

According to one embodiment, a method of determining one or more properties of a biological and/or chemical reaction from a data set representing an amplification process of the reaction is provided. A set of data points representing a curve having a baseline portion and a growth portion is received. Each data point represents a physical quantity of a substance during an amplification process. A processor calculates a first function that approximates the set of data points. One or more parameters are extracted from the first function. The processor uses the one or more parameters to calculate a second function that approximates the set of data points. One or more properties of the biological and/or chemical reaction are determined using the second function.

According to another embodiment, a method of determining a baseline region for an amplification curve resulting from an amplification process of a biological and/or chemical reaction is provided. A set of data points representing a curve having a baseline portion and a growth portion is received. A processor determines a function that approximates the set of data points. A first derivative of the function is calculated to obtain a first derivative function. A processor determines an end of a baseline region by integrating the first derivative function from a respective point to a fixed location of the first derivative function to obtain a respective integrated area. A point whose integrated area is within a specified range is selected as the end of the baseline region. A beginning of the baseline region is also determined.

According to yet another embodiment, a method of determining a reference value of a biological and/or chemical reaction from a data set representing an amplification process of the reaction is provided. A set of data points representing a curve having a baseline portion and a growth portion is received. A processor determines a function that approximates the set of data points. A processor determines a function that approximates the set of data points. The processor calculates at least two derivatives of the function. A respective time in the amplification process where each derivative has a maximum value is identified. The reference value of the biological and/or chemical reaction is calculated as a weighted average of the respective times.

In one embodiment, data representing amplification in the collected data is distinguished from data representing a jump or other error by checking whether a slope of the data or a function approximating the data has a slope grater than a threshold. In another embodiment, a modified sigmoid function containing a drift term is used to approximate the data representing the amplification process.

Other embodiments of the invention are directed to systems and computer readable media associated with methods described herein.

A better understanding of the nature and advantages of the present invention may be gained with reference to the following detailed description and the accompanying drawings.

DETAILED DESCRIPTION

The present invention provides techniques for processing and analyzing results from an amplification reaction, for example, to determine a number of different properties of the reaction. Various embodiments are particularly useful for analyzing data from PCR amplification processes to identify, for example, a baseline, a quantification value (e.g. a Ct value), and different regions of behavior from a functional form of the data. It should be appreciated, however, that the teachings of the present invention are applicable to processing any data set or curve that may include noise, and particularly curves that should otherwise exhibit growth (amplification) such as a bacterial growth process.

I. Amplification Curves

Amplification (growth) curves show when a quantity has increased over time. Such curves can result from polymerase chain reactions (PCR). Data for a typical PCR growth curve can be represented in a two-dimensional plot, for example, with a cycle number defining the x-axis and an indicator of accumulated growth defining the y-axis. Typically, the indicator of accumulated growth is a fluorescence intensity value resulting from fluorescent markers. Other indicators may be used depending on the particular labeling and/or detection scheme used. Examples include luminescence intensity, bioluminescence intensity, phosphorescence intensity, charge transfer, voltage, current, power, energy, temperature, viscosity, light scatter, radioactive intensity, reflectivity, transmittance and absorbance. The definition of cycle can also include time, process cycles, unit operation cycles and reproductive cycles.

Figure 1:
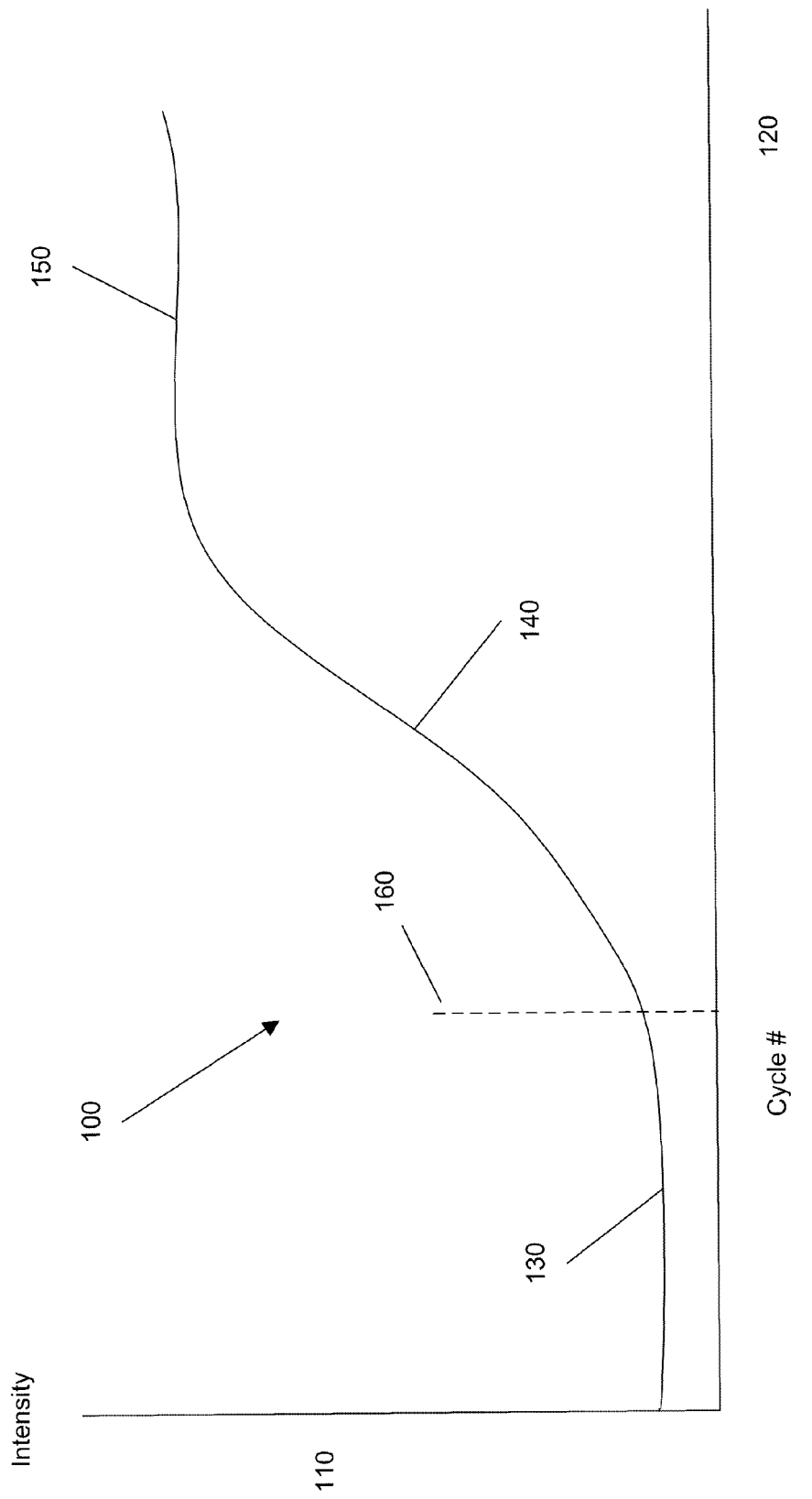
FIG. 1 shows an example of a PCR amplification curve.

FIG. 1 shows an example of a PCR curve 100, where intensity values 110 vs. cycle number 120 are plotted for a typical PCR process. The values 110 may be any physical quantity of interest, and the cycle number may be any unit associated with time or number of steps in the process. Such amplification curves typically have a linear portion (region) 130 followed by a growth (amplification) portion 140 and then by an asymptotic portion 150, as shown in FIG. 1. There also might be additional types of behavior such as downward curving data. A growth portion may have exponential, sigmoidal, high order polynomial, or other type of logistic function or logistic curve that models growth.

To understand the experimental process involved, it is important to identify the position and shape of growth portion 140. For example, in a PCR process, it may be desirable to identify the onset of amplification, which occurs at the end 160 of the baseline portion (linear portion 130). Additionally, the analysis of the shape of growth portion 140 often includes "baselining" or subtracting out linear portion 130 from PCR curve 100.

Figure 2:
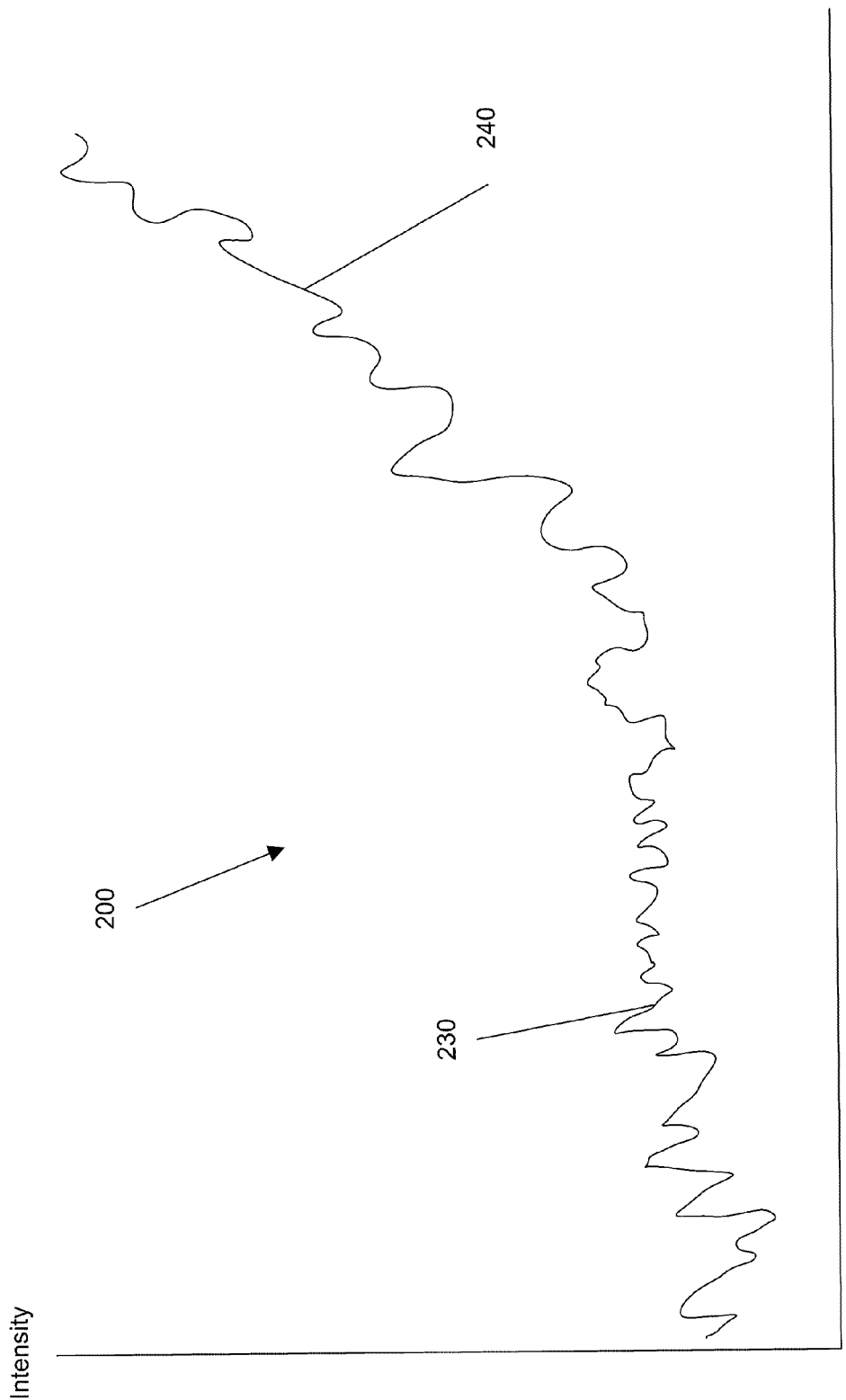
FIG. 2 shows an example of raw data measured from an amplification process.

FIG. 2 illustrates a real-time PCR curve 200 that exhibits amplification. Initially, the data exhibits linear behavior in region 230 and in later cycles there is amplification in region 240. When FIG. 2 is contrasted with FIG. 1, it is clear that noise and other variability that is often present in real-time PCR curves can make any analysis of data to determine underlying properties of the reaction much more difficult than the more ideal model shown in FIG. 1.

The curves may be analyzed for many different purposes. Some of the purposes are described herein.

II. Overview of Analysis of Amplification Curves

Figure 3:
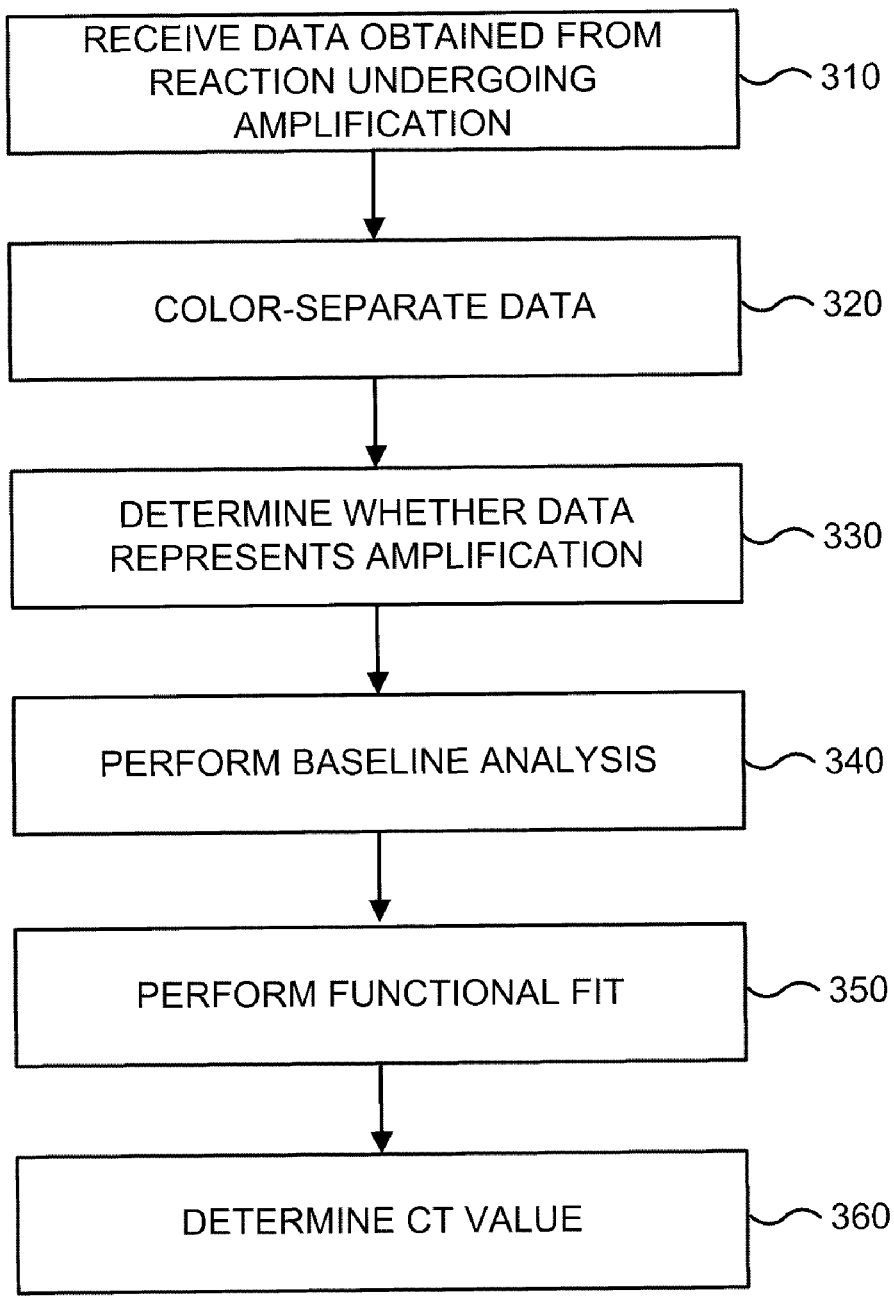
FIG. 3 is a flow diagram illustrating a method of analyzing data points from an amplification reaction according to an embodiment of the present invention.

FIG. 3 is a flow diagram illustrating a method of analyzing data points from an amplification reaction according to an embodiment of the present invention. Many of the steps in FIG. 3 are optional depending on the particular needs of an embodiment. Additionally, many of the various steps outlined in FIG. 3 can be carried out independently of other steps. For example, the baseline analysis shown in FIG. 12 can be conducted independently of any Ct determination. Specific methods of carrying out some of the steps in FIG. 3 are described later with respect to other figures.

At step 310, raw data taken from a biological or chemical reaction undergoing amplification is received for analysis. In some embodiments, the raw data represents various wavelengths of light that have been collected from the reaction. In one embodiment, the data is an intensity of light measured after each cycle of the reaction. The raw data, e.g., in the form of a set of fluorescence values per cycle, may be loaded into a memory so that it may be analyzed.

At step 320, these wavelengths of light can be separated according to their color before further analysis is conducted. In one embodiment, a per-well normalized color separation matrix is generated which can be derived from the instrument calibration data. The matrix can depend specifically upon the dyes loaded into that well. In one aspect, matrix operations, such as matrix inverse or singular value decomposition, are used to calculate color-separated data from the raw data. Color-separated data can be output as a set of curves, each of which is identified by the dye, step number, and the well index. An amplification curve exists for each color, as well as for each well sample and step. These output curves may have the baseline subtracted before being displayed to a user.

At step 330, the color-separated raw data is analyzed to determine whether the data indicates that amplification has occurred in the underlying reaction. Various analyses may be performed to determine whether amplification has occurred. Examples of analyses that determine no amplification include if the curve is too short, if the standard deviation of the data values in the curve is sufficiently small, if a functional fit of the data points in the curve has a negative slope, and if the difference between the data and its linear fit switches sign enough times relative to the number of points. US Patent Application 2006/0271308, incorporated by reference for all purposes, discloses a method for determining whether the data exhibits statistically linear behavior in order to distinguish linear data from data that would represent amplification. In some embodiments, a maximum amplitude slope bound analysis is conducted to determine whether the data indicates that an amplification has occurred, which is described in more detail later.

If no amplification has occurred, some embodiments will not conduct any further analysis on the data. If amplification has occurred, some embodiments will continue with method 300.

At step 340, a baseline analysis is conducted. A baseline generally relates to effects that do not relate to the amplification process. For example, offsets, drifts, noise, or other artifacts may be present in an intensity signal, and are not a result of the underlying amplification process. The baseline analysis may be performed in various ways. In some embodiments, the baseline analysis is conducted by creating a probability distribution function from a functional approximation (fit) of the raw data to determine the end of the baseline within a specific confidence level. This baseline analysis is discussed in more detail later in this disclosure. In one embodiment, a sigmoid function may be used as the functional approximation of the raw data.

At step 350, a functional fit is performed to create a functional approximation that closely matches the raw data. In some embodiments, a functional fit from step 340 may be used as the fit for step 350. In other embodiments, a new functional fit is performed, which may be based on a previous functional fit. Such a multi-stage fit is described in more detail below. In one embodiment, a modified sigmoid function is used as the functional approximation.

At step 360, some embodiments use the functional approximation from step 350 to determine a Ct value. As discussed above, a Ct value for an amplification curve can be used to calculate some quantification, in either absolute or relative terms, of a specific target molecule in the reaction. In some embodiments, the Ct value is determined using a weighted-average of the two derivatives of the functional approximation.

In some embodiments where a result of step 330 suggests non-amplification, method 300 can set an end of a baseline region to the last cycle and/or set the Ct value to the intersection of the curve with its mean value.

III. Determining Whether Amplification Exists

As described above with respect to step 330, an analysis may be made as to whether the data represents an amplifying reaction. In one embodiment, a maximum amplification slope bound analysis is performed.

Figure 4:
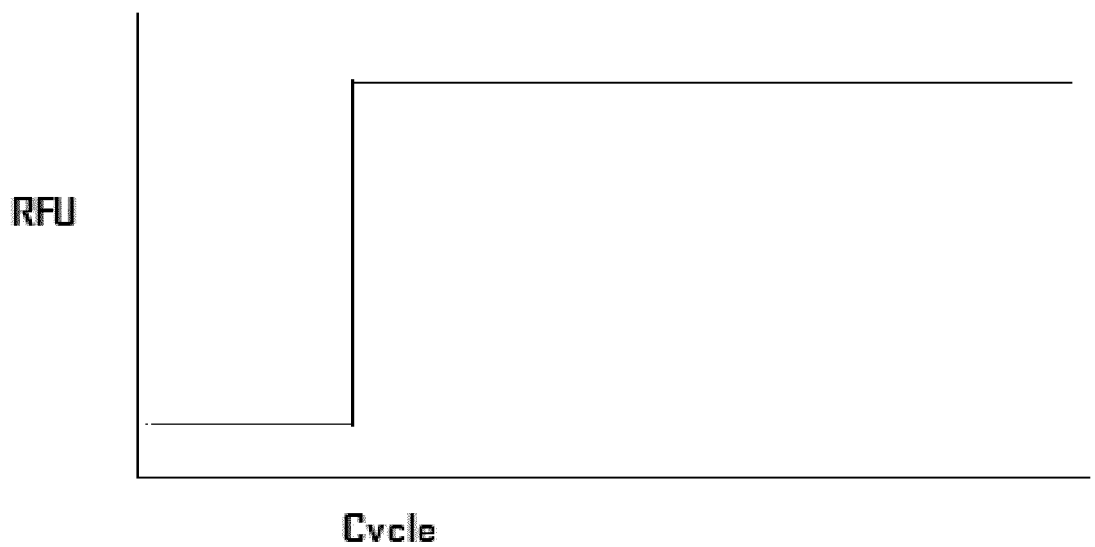
FIG. 4 is an illustration of a data curve representing a jump rather than actual amplification.

In a number of cases, there are jumps in data due to the instrument being hit or disturbed during a run. In this case, the data can display a sharp jump that appears to represent amplification, but is in fact an artifact of an error. An extreme example of a curve that displays this behavior is shown in FIG. 4. In FIG. 4, RFU refers to relative fluorescence and cycles refer to cycles of amplification of the PCR reaction, or any process displaying amplification type behavior. Embodiments use a maximum allowed slope for real amplification to distinguish between real amplification and any artifact, such as a jump in the data resulting from an error.

Figure 5:
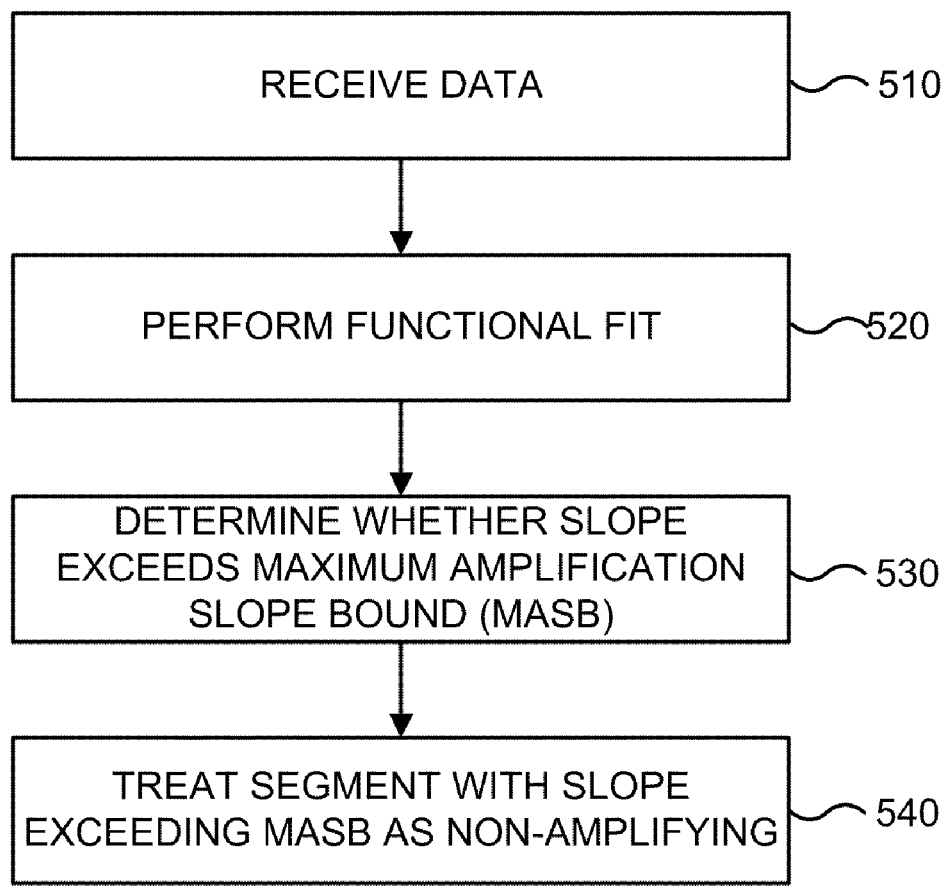
FIG. 5 is a flow diagram illustrating a method of determining whether a segment of a data curve shows amplification according to an embodiment of the present invention.

FIG. 5 is a flow diagram illustrating a method 500 of determining whether a segment of a data curve shows amplification according to an embodiment of the present invention. In various embodiments, method 500 may be performed prior to baselining, after baselining, or as part of a baselining procedure. For example, the part of the curve from the start to the end of the baseline may be analyzed to identify amplification behavior; and if there is amplification behavior, then method 500 may be applied.

At step 510, data taken from a biological or chemical reaction undergoing amplification is received for analysis. In some embodiments, the data may be color separated. The data received typically have a baseline portion and a growth portion.

At step 520, a functional fit is conducted using the data to obtain a functional approximation of the data. This functional approximation can be used by some embodiments to determine various characteristics of the underlying reaction. In some embodiments, a sigmoid function is used for the functional approximation. In other embodiments, a functional fit may be performed only for a portion of the data.

At step 530, an analysis of the functional approximation is conducted to determine whether a slope of the functional fit exceeds the maximum amplification slope bound (MASB). The analysis of the slope of the functional fit may be performed for every point of the data curve.

At step 540, for those locations (e.g. segments) where the slope exceeds the maximum amplification slope, the data may be treated as non-amplifying. In one embodiment, if the analysis of method 500 removes all of the possible amplification regions, then the data curve may be classified as non-amplifying. In another embodiment where an amplification region does exist after the jump, then a start of the baseline region may be set just after the jump.

One embodiment for the derivation of the maximum slope is as follows. In one aspect, the equations below show that the slope of a real amplification curve is bounded above by the slope of an ideal, purely exponential amplification curve of constant maximal efficiency.

Consider amplification, where $y_n$, represents the baselined data and $E_N$ represents the amplification efficiency at cycle N.

$$y_{N+1} = (1+E_N)y_N$$

Since the behavior is exponential, derivatives can be approximated by difference in ln space (ln is natural logarithm). As a result, the derivative can be written as:

$$\ln(y_{N+1}) - \ln(y_N) = \ln(1+E_N)$$

Using the Mean Value Theorem, it can be shown that:

$$\ln(y_{N+1}) - \ln(y_N) = \frac{d\ln(y(N))}{dN}$$

where N is evaluated at some value $N=N^*$ and $N<N^*<N+1$.

The equations derived from the difference of the natural log of the baselined data and the Mean Value Theorem can then be combined to obtain:

$$\frac{d\ln(y(N^*))}{dN} = \ln(1+E(N))$$

where y and E can be defined everywhere as continuous functions. Note that the left and right hand sides of the equation are evaluated at different values, N and $N^*$. Since $E(N)<1$, the right hand side of the equation is rigorously bounded above by $\ln(2)$.

Since the right hand side is now independent of N, the * can be dropped. The result is:

$$\frac{d\ln(y(N^*))}{dN} = \left(\frac{1}{Y(N)}\right)\left(\frac{dy(N)}{dN}\right) < \ln(2.0)$$

Which in turn yields:

$$\left(\frac{dy(n)}{dN}\right) < \ln(2.0) * y(N)$$

This expression can be evaluated for a functional fit (e.g. a regression function fit) to the data as a test to determine whether the inequality is satisfied. If the inequality is satisfied, the data represents possible amplification. If the inequality is not satisfied, then the data contains an artifact and can be handled in an appropriate manner. For example, this test can be used as a part of the initial tests used to determine if the collected PCR data represents a reaction that has undergone amplification. Other embodiments can use this analysis for other purposes as well.

IV. Baselining

Figure 6:
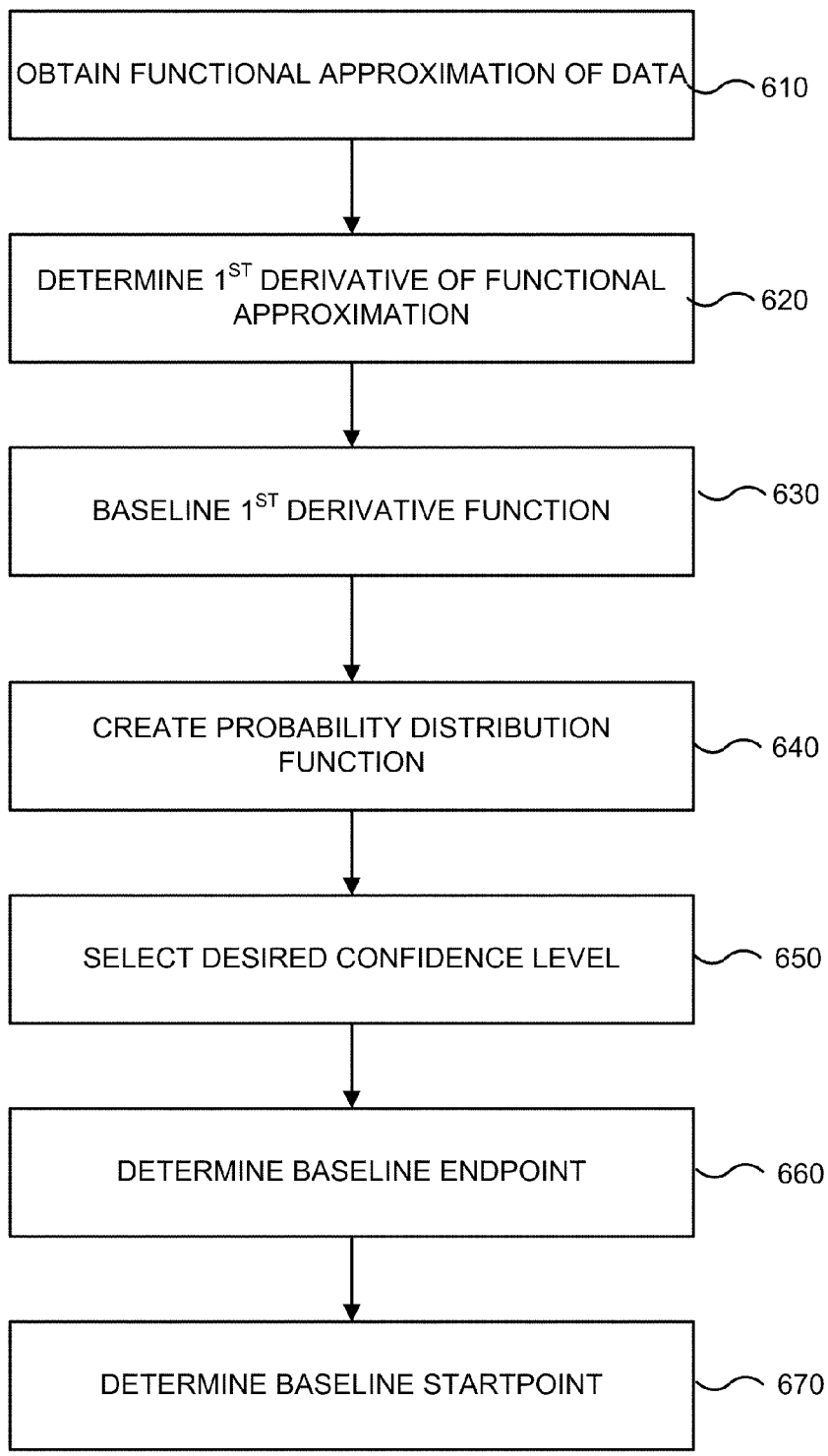
FIG. 6 is a flow diagram illustrating a method of determining a baseline region of an amplification curve according to an embodiment of the present invention.
Figure 7:
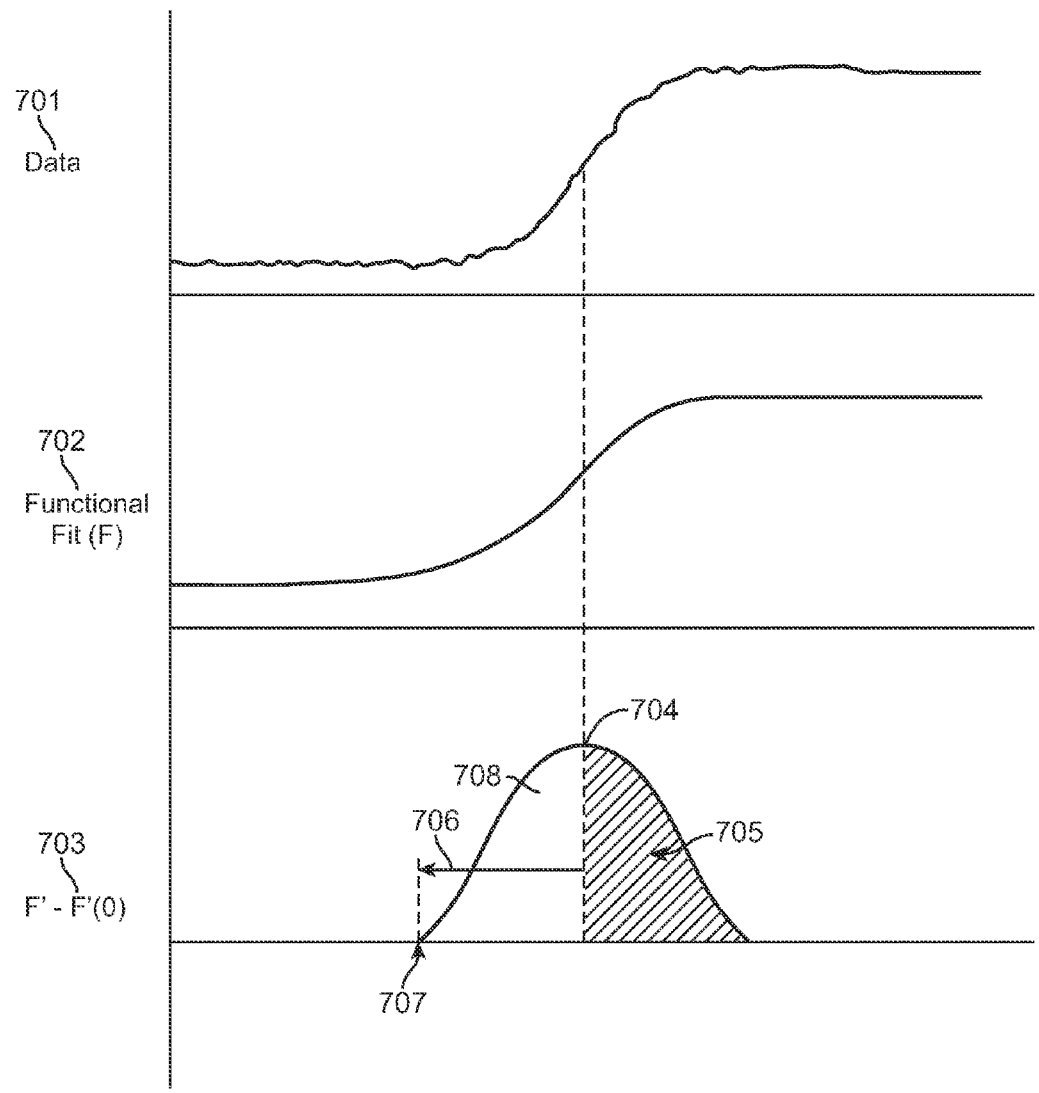
FIG. 7 are plots of amplification data and curves resulting from a baselining method according to an embodiment of the present invention.

FIG. 6 is a flow diagram illustrating a method of determining a baseline region of an amplification curve according to an embodiment of the present invention. A graphical representation of method 600 is illustrated in FIG. 7.

At step 610, a functional approximation (fit) to the data is obtained. In some embodiments, a pure sigmoid function can be used for the functional fit. The sigmoid provides a functional approximation to the curve defined by the collected data. An example of the raw data 701 and its functional approximation 702 is illustrated in FIG. 7.

At step 620, the first derivative F' of the functional fit is determined. The first derivative may be determined in any number of ways, which may be dependent on the type of functional fit that was performed.

At step 630, the value of the derivative at the start of the curve, F'(0), can then be subtracted from the curve itself so that the derivative function is baselined. An example of a baselined first derivative function is shown at 703.

At step 640, a probability distribution function is created, for example, a distribution which defines a probability that a point is within the amplification (growth) region. In this manner, the start of the amplification region may be determined, and thus the end of the baseline region can be calculated.

In one embodiment, the probability distribution function relates to the area under the $1^{st}$ derivative function in the non-crosshatched area 708. The region after the peak of the derivative function is truncated as illustrated by area 705. Thus, area 705 is not used in one embodiment of the baseline analysis. The region from the start of the derivative function to the peak 704 (which occurs at the inflection point) of the derivative function is used for further analysis. The baselined derivative function is then divided by area defined under its curve (e.g. as a normalization), yielding a new function that may be interpreted as a probability distribution of whether a given point is in the amplification region. The probability distribution function has a maximum (100%) at the inflection point of the original curve and decreases monotonically toward 0% at the beginning of the curve.

At step 650, a confidence level for the start of the amplification region is selected. In some embodiments, the confidence relates to an amount (e.g. a percentage) of area under the baselined derivative function. For example, the start of the baseline region can be interpreted as occurring at a point where the integrated area is relatively small. Such a point would occur when the point has a small probability (e.g. 3–0%) of being in the amplification region as then that point would no longer be in the baseline region.

In one embodiment, a probability that a point is within the amplification region can be interpreted inversely (e.g. subtracted from 100%) so that the confidence level of the start of the amplification region can be taken to be near 100%. In one embodiment, the value of the confidence level as a practical matter, is desired to be between 90% to 97%. A value of 100% would actually provide too low of a cycle number for the start of the amplification region since that point might be near the beginning of the whole curve. A value of less than 90% would provide too high of a value since that point would quite likely to be inside the amplification region.

At step 660, the end of the baseline endpoint is determined by the point at which the confidence level is achieved. In one embodiment, to determine the start of the amplification region (end of the baseline region) within the desired confidence level, the area of the probability distribution function from the peak 704 is integrated going backwards toward the beginning of the function, as illustrated by 706, until the area matches the selected confidence level (e.g. at fractional cycle value x). In FIG. 7, this point is marked at 707. The area under the probability distribution function, from the peak 704 to point 707 is equal to the selected confidence level.

In another embodiment, the curve may be integrated from the start until the confidence level is reached, which, e.g., may be interpreted as being between 3%-10%. This value minus 100% may be used to conform to the manner in which the confidence level was selected (e.g. being near 100%).

This point, 707, can be used as a credible bound on the region in which amplification is expected to have occurred. This cycle value can be interpreted as the end of the baseline.

At step 670, once the end of the baseline has been determined, the start of the baseline can be determined. In one embodiment, the portion of the curve from the start of the curve to the end of the baseline (an extracted portion) is analyzed to determine the start of the baseline. If the extracted portion is sufficiently linear, then the start of the baseline is set to the start of the curve.

In one aspect, sufficient linearity is measured as the degree that the data points can be fit to a line. For example, in a least squares fit, the standard deviation of the data points from the fitted line may be used as a measure of the linearity. The error from the linear behavior can be compared to a threshold value to determine if linearity does exist.

The sufficiently linear region can be treated as a region of non-amplification. In one embodiment, the first cycle is removed from the baseline region to eliminate problems common to starting the PCR process as the instrument settles.

If the extracted portion of the curve is not sufficiently linear, then additional analysis can be carried out to determine the start of the baseline. In one embodiment, the additional analysis consists of repeatedly removing or truncating the leading points of the extracted portion of the curve until the leading region is non-amplifying or a certain maximum number of truncations is reached. The maximum slope analysis disclosed above may additionally be repeatedly used to determine whether there is a jump inside the baseline region, such that the start of the baseline may be set immediately after the jump location.

Below is a more detailed mathematical description of an embodiment of this baselining method.

The first step is to apply a functional fit to the raw data. The first step of the functional fit is to select a functional approximation to be used to model the data. In one embodiment, a sigmoid function is used for this purpose.

Next, a set of initial regression (fitting) parameters to be used in the selected functional approximation of the data need to be defined. The regression parameters used below are: $a_0$, $a_1$, $a_2$, $a_3$. The set of parameters below is an example of one set of parameters that has been empirically determined to work well for a variety of data sets. For input vectors (x,y) of values, where y=RFU and x=cycle, the parameters can be seeded as follows: $a_0$=y[1]; $a_1$=y.Max−y.Min; $a_2$=x.Length/2; $a_3$=1.0.

An example of a sigmoid regression function using these regression parameters is:

$$f = a_0 + \frac{a_1}{D},$$

where $$E(x) = \frac{(a_2 - x)}{a_3}, \ h(x) = \exp(E(x)), \text{ and } D(x) = 1 + h(x).$$

Using this regression function, the first derivative of the function can be calculated to be:

$$\frac{df}{dx} = \frac{a_1}{a_3} \frac{h}{D^2}$$

and the second derivative can be calculated to be:

$$\frac{d^2 f}{dx^2} = \left(\frac{a_1}{a_3^2}\right) \frac{h}{D^3}(h - 1)$$

The maximum $1^{st}$ derivative is the x value defined by the zero of the second derivative equation.

The probability of a point being in the amplification region is computed to be:

$$P = \frac{\frac{df}{dx} - \frac{df}{dx}(0)}{\text{Normalization}}$$

In the non-crosshatched region, we integrate to the left from the inflection point, I, to find the boundary, $\mu$, of the 95% confidence region for being at the start of the amplification region.

$$\frac{\int_\mu^I P}{\int_0^I P} = c$$

Substituting P into the above expression provides:

$$f(I) = f(\mu) - \frac{df}{dx}(0)[I - \mu] = c\left[(f(I) - f(0)) - \frac{df}{dx}(0)I\right]$$

Substituting the pure sigmoid into this expression yields:

$$\mu = a_2 - a_3 \ln\left[\left(\frac{1}{\Gamma + \beta\mu}\right) - 1\right] \equiv H(\mu),$$

where $$\beta = \frac{\frac{df}{dx}(0)}{a_1} \text{ and } \Gamma = \frac{(1-c)}{2} + \frac{c}{D(0)} - (1-c)\beta a_2.$$

Next, the following functions are iterated to determine the start of the baseline:

$\mu_0 = H(0)$ $\mu_{N+1} = H(\mu_N)$

These functions are iterated until it converges to the desired value of the endpoint of the baseline region.

Figure 8:
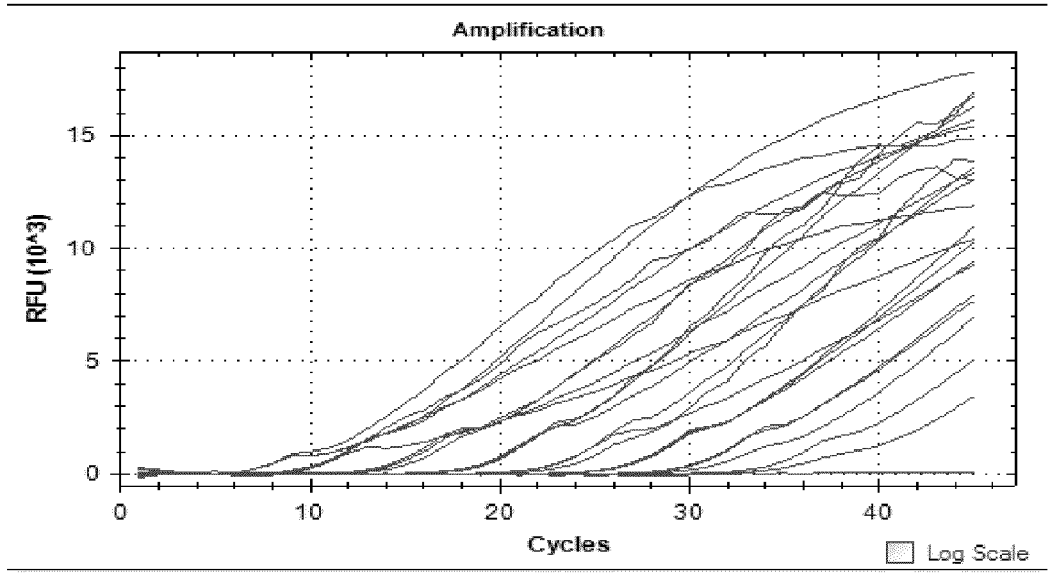
FIG. 8 is an illustration of many PCR curves that have been baselined using an embodiment of the present invention.

FIG. 8 illustrates the effectiveness of the above baselining method. In FIG. 8, many different data sets, including many noisy data sets, are effectively baselined using the above method. As is clearly visible, the linear regions prior to amplification have been identified such that when subtracted off the curve, the linear regions lie flat against the x-axis (cycles) of the graph.

V. Multi-Stage Functional Fit

As mentioned above, a functional approximation of the data values obtained from the amplification reactions can be used for multiple purposes, such as baselining and identifying Ct values. One functional form that has been used is a sigmoid function of the form $1/(1+e^{-1})$. However, such a functional form can miss physical characteristics of an amplification reaction. Accordingly, some embodiments use a modified sigmoid function (described below) that uses a drift term, which can account for a variably drifting baseline, as well as other characteristics that a sigmoid function can miss.

However, if used with default parameters, the higher resolution function may be less stable in providing a good functional fit. For example, higher resolution functions, such as the modified sigmoid function discussed above, are frequently much more sensitive than lower resolution functions to the initial starting parameters used to create the function. As a result, using default parameters for these higher resolution functions may not yield good results. In other words, the higher resolution function may not effectively reduce the error between the functional approximation of the data and the data itself when default starting parameters are used.

The error present in any regression function can be minimized using an algorithm, for example a Levenberg-Marquardt algorithm. It minimizes the error, i.e. the difference between a fit function and the actual data, as measured by the equation:

$$\text{Delta} = \sum_{i=1}^{N} [y_1 - f(x_i, \overline{P})]^2$$

where P is a vector of regression parameters to be varied until an adequate fit is achieved.

Traditionally, it is a combination of Gauss-Newton and Gradient Descent methods, whereby the algorithm adjusts to which method to use during the calculation depending upon the nature of the error.

When the modified sigmoid functional form is used, it may be difficult to obtain convergence with the minimization algorithm. Accordingly, in one embodiment, a first sigmoid functional fit is performed to obtain parameters (seed values) for the modified sigmoid functional form. In another embodiment, the modified sigmoid functional fit can be calculated without seed values from another functional fit.

Figure 9:
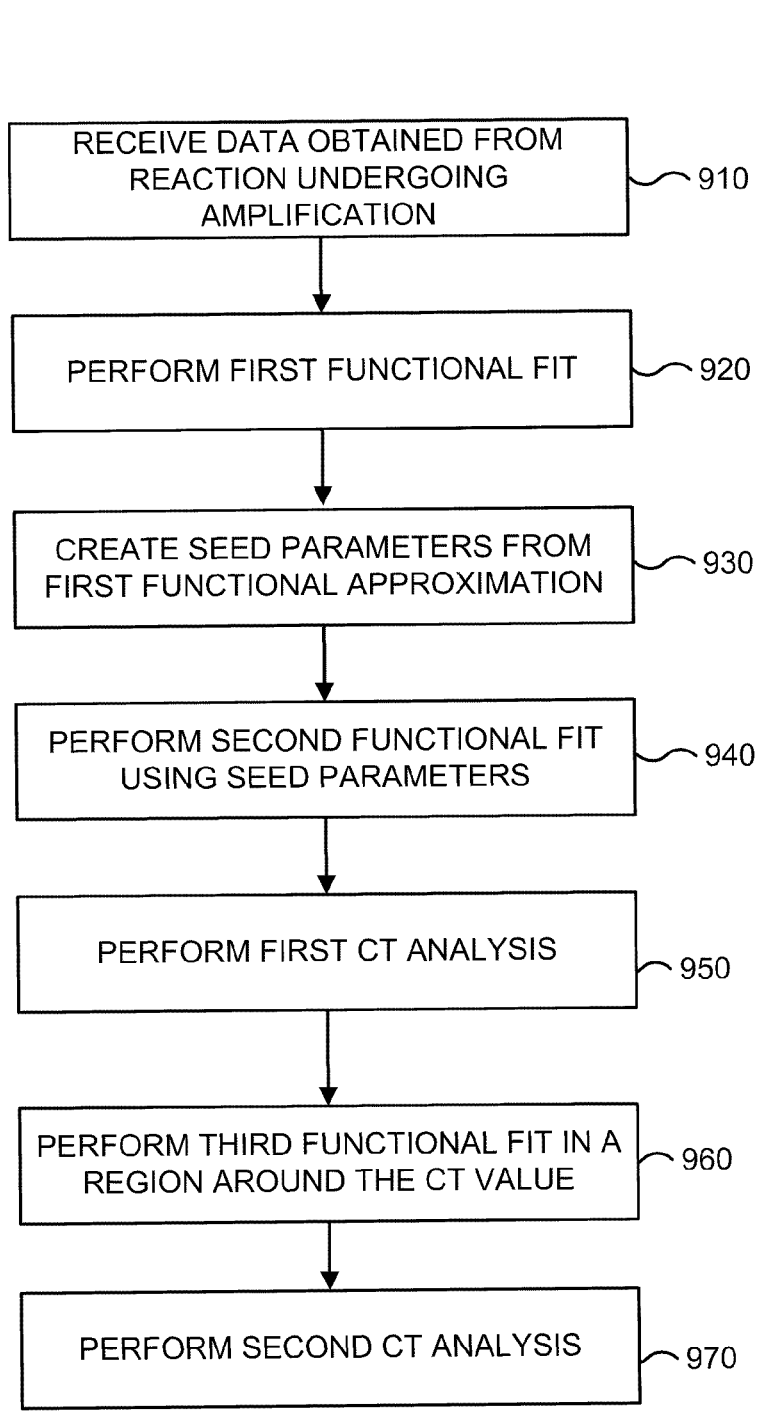
FIG. 9 is a flow diagram illustrating a method of analyzing an amplification curve by performing a multi-stage functional fit to determine properties of the amplification reaction according to an embodiment of the present invention.

FIG. 9 is a flow diagram illustrating a method of analyzing an amplification curve by performing a multi-stage functional fit to determine properties of the amplification reaction according to an embodiment of the present invention. As shown, method 900 uses three stages of functional fits while other embodiments may use more or less stages of analysis. Although examples using sigmoid and a modified sigmoid function are provided, the multi-stage functional fitting may use other functional forms.

In the below description, the terms "low resolution" and "high resolution" refer to the order of the functional fits, with a higher resolution fit occurring after a lower resolution fit. These terms can also correspond to a degree of accuracy that the functional approximation of the data maps to the underlying raw data. Thus, each stage of the analysis can build upon the previous stage of the analysis to create a more accurate functional approximation the data.

At step 910, data is received from the amplification reaction. This data may be of any suitable form, e.g., as mentioned herein.

At step 920, a first functional fit of the amplification data is determined. The first functional fit is of a low resolution. For example, the data curve may be fit by a pure sigmoid function. A low resolution function, such as a sigmoid model, is typically less sensitive to the initial seed parameters than a higher resolution function, such as a modified Sigmoid regression function. As a result, a pure sigmoid function works well using default initial parameters.

In one aspect, this function can be used to conduct any analysis that does not benefit much from a high-resolution function. An example analysis that can be conducted using this first functional fit is a baseline analysis.

At step 930, the low resolution function is used to create the seed parameters for the next stage of the multi-stage analysis. In one embodiment, the seed parameters are initial values for the parameters of the higher resolution function.

At step 940, a second functional fit uses the seed parameters to obtain a higher resolution fit (e.g. a regression function). In one aspect, using seed parameters from the lower resolution function can provide better initial values for the higher resolution fit. With better initial values, convergence of a fitting method (e.g., as mentioned above) can be obtained easier and more reliably.

Performing a multi-stage functional fit can also provide robustness in the final functional fits that are obtained. A key measure of robustness is the repeatability of the determination of characteristics of the underlying reaction. The higher-resolution function can be used to calculate parameters such as the Ct value for the underlying reaction. The repeatability can be measured using the Ct standard deviation for replicates. A robust regression engine can also converge more reliably to provide a smaller Ct standard deviation, where convergence may be measured by whether the error of the fit to the actual data can be made sufficiently small.

At step 950, the second functional fit is used to determine the Ct value for the amplification reaction. In one embodiment, the Ct value is determined as the cycle number that the second functional fit (e.g. a modified sigmoid function) crosses a threshold value. In another embodiment, a weighted average of derivatives of the functional approximation (fit) is used as the Ct value.

At step 960, a third functional fit is performed in a region defined by the Ct value obtained in step 950. For example, the Ct value calculated from the second functional approximation can be used to define the centroid of a region encompassing the amplification region. The third functional fit can then be made as an approximation to the data points in this region. In one embodiment, the width of the region defined by the centroid is twice that of the cycle width between the centroid and the start of the growth (amplification) region.

In one embodiment, this third functional fit is carried out on just the amplification region because of variability in the global behavior of amplification curves. This variability reflects possible instrument bias due to such factors as spatial alignment issues. Since the second functional fit may be global and reflect the overall behavior of the entire amplification curve, this bias can be reflected in the calculated Ct value from the second regression. In order to reduce this effect, a very high resolution regression can be carried out on a window encompassing only the amplification region. This excludes variability reflected in the leading part of the curve, as well as the tails of the curves, where chemistry is often being depleted and alignment issues arise.

In some embodiments, the third functional fit can be a polynomial regression. In one embodiment, a $6^{th}$ order polynomial functional fit is applied to the amplification region. The order of a polynomial applies to the value of the exponent of the leading term of the polynomial.

At step 970, the third functional fit can then be used to determine characteristics, such as the Ct value, to an even greater degree of accuracy. This process of using a lower-resolution regression to seed the starting parameters of a higher resolution regression function can be repeated as many times as needed. In each iteration, the previous regression function is used to determine the seed values for an even higher resolution regression function. If, for some reason, the higher-resolution function cannot be generated using the initial seed parameters from the first regression function, a priori estimates for the starting parameters can be used instead.

In one embodiment, the high resolution functional approximation used for the second functional fit is a modified sigmoid function defined as follows:

$$f = a_0 + \frac{1}{D}\left[a_1 + \left(\frac{a_4}{D}\right)\ln\left(\frac{D}{h}\right)\right],$$

where $$E = \frac{(a_2 - x)}{a_3}, h = \exp(E), D = 1 + h, \text{ and } \alpha = \frac{2a_4}{a_1}.$$

In this equation, the term $$\left(\frac{a_4}{D}\right)\ln\left(\frac{D}{h}\right)$$

is an internal linear drift term, representing a variably drifting baseline, that is a modification from a standard sigmoid function. This term improves the fit between the functional approximation of the data and the data itself by multiple standard deviations by better representing the actual behavior seen in amplification data.

Default initial regression parameter seed values for input vectors (x,y) may be: a0=Parameters[0]=y[1]; $a_1$=Parameters[1]=y.Max-y.Min; $a_2$=Parameters[2]=Parameters[3]=1.0; and $a_4$=Parameters[4]=y.Mean-y[1].

However, as mentioned above, these default values may not produce an accurate amplification data model. In that case, the values used for these variables can be obtained from the pure sigmoid functional fit, which may be obtained from step 920. For example, the values for $a_0$-$a_3$ may be taken directly from the final values for sigmoid functional fit. In one aspect, the seeds may be determined in this fashion because of the similar functional forms.

The $1^{st}$ and $2^{nd}$ derivatives with respect to x are as follows:

$$\frac{df}{dx} = \left(\frac{a_1}{a_3 D^2}\right)\left[h + \frac{\alpha}{2D} + \alpha\left(\frac{h}{D}\right)\ln\left(\frac{D}{h}\right)\right]$$

$$\frac{d^2 f}{dx^2} = \left(\frac{a_1 h}{a_3^2 D^4}\right)\left[h^2 - 1 + \frac{5\alpha}{2} + \alpha(2h-1)\ln\left(\frac{D}{h}\right)\right]$$

The maximum $1^{st}$ derivative is the x value defined by the zero of the $2^{nd}$ derivative.

The $3^{rd}$ derivative with respect to x is:

$$\frac{d^3 f}{dx^3} = \left(\frac{a_1 h}{a_3^3 D^5}\right)\left\{\begin{array}{c}\left[h^3 - 3h^2 + \left(-3 + \frac{19\alpha}{2}\right)h + \left(1 - \frac{7\alpha}{2}\right)\right] + \\ \alpha\ln\left(\frac{D}{h}\right)[4h^2 - 7h + 1]\end{array}\right\}$$

The maximum $2^{nd}$ derivative location is the x value defined by the appropriate zero of the $3^{rd}$ derivative.

The $4^{th}$ derivative with respect to x is:

$$\frac{d^4 f}{dx^4} = \left(\frac{a_1 h}{a_3^4 D^6}\right)\left\{\begin{array}{c}\left[\begin{array}{c}h^4 - 10h^3 + \left(\frac{65\alpha}{2}\right)h^2 + \\ (10 - 40\alpha)h + \left(-1 + \frac{9\alpha}{2}\right)\end{array}\right] + \\ \alpha\ln\left(\frac{D}{h}\right)[8h^3 - 33h^2 + 18h - 1]\end{array}\right\}$$

The maximum $3^{rd}$ derivative location is the x value defined by the appropriate zero of the $4^{th}$ derivative. By identifying the maximal derivative locations, in one embodiment, this information may be used to determine the Ct values.

Figure 10:
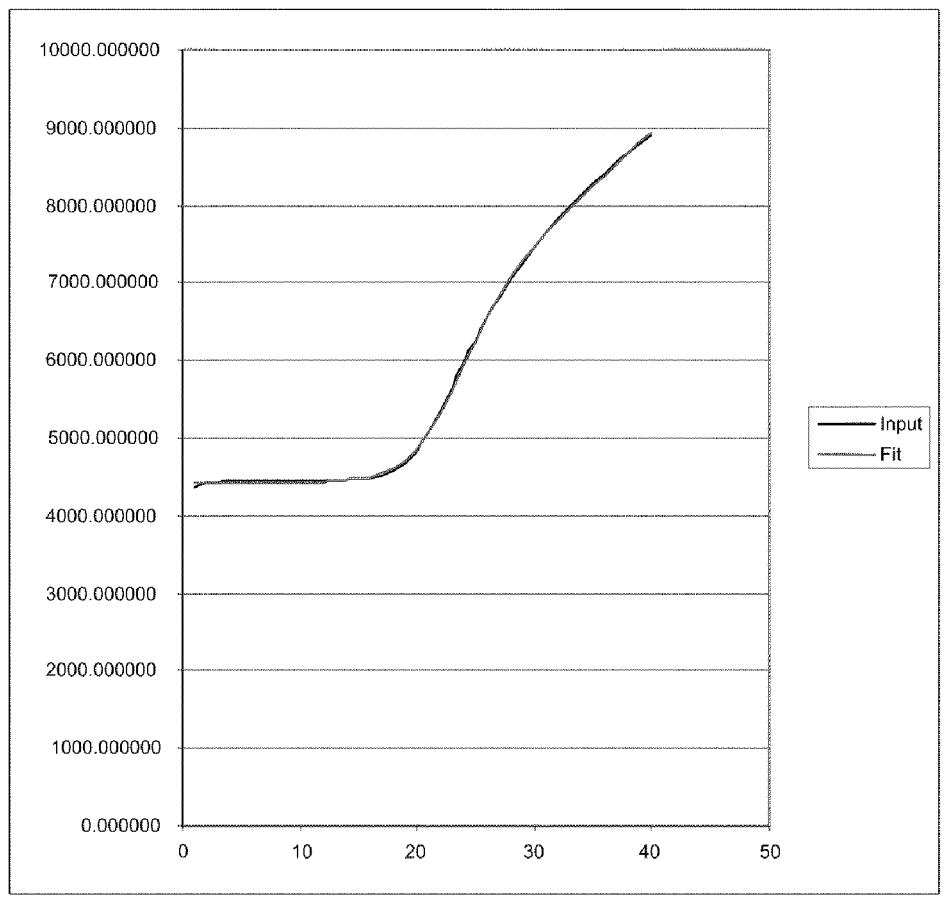
FIG. 10 is an illustration of the fit between a modified sigmoid function and PCR data according to one embodiment of the present invention.

FIG. 10 shows an example of the high resolution modified sigmoid regression function fitted against raw data. Note that the fit is globally excellent for this example because the two lines are nearly indistinguishable from each other.

VI. Calculation of Ct Value—Weighted Maximum Derivative Method

There are a number of possible methods for selecting the Ct value for a reaction undergoing amplification. Each method has certain advantages and disadvantages. The Ct value may be determined after a single stage, after each single stage, or after multiple stages of performing functional fits.

The Ct value represents a point on a curve, a fractional cycle number that is similar in some property to that point on another curve. In various embodiments, the Ct value can be the fractional cycle number where an intensity signal reaches a target threshold, where a certain amplification value is reached, where some concentration value is reached, where the maximum of some derivative value or combination of derivative values is reached, or some other property that represents a value of the curve or shape of the curve.

The Ct value can allow one to compare the relative level of amplification between different curves representing different unknown starting quantities, or a comparison with a standard of known, absolute starting quantity. The first is known as relative quantitation, while the latter is known as absolute quantitation.

In one embodiment of the present invention, the Ct value is selected as the number of cycles (which may be a fractional number) at the maximum of the $2^{nd}$ derivative of a functional approximation to the amplification curve. This value gives excellent quantitation of the Ct value, but it can lead to a Ct value that is overly high. It can also lead to an overly high efficiency value.

In another embodiment, the Ct value is selected as the number of cycles (which may be a fractional number) at the maximum $3^{rd}$ derivative location of a functional approximation to the amplification curve. This method yields excellent Ct values that are roughly two cycles before the maximum $2^{nd}$ derivative location. This method also yields good, but not excellent efficiency values. However, the quantitation of the Ct value at the $3^{rd}$ derivative location, while acceptable, is not as good as the quantitation of the Ct value at the $2^{nd}$ derivative location.

Figure 11:
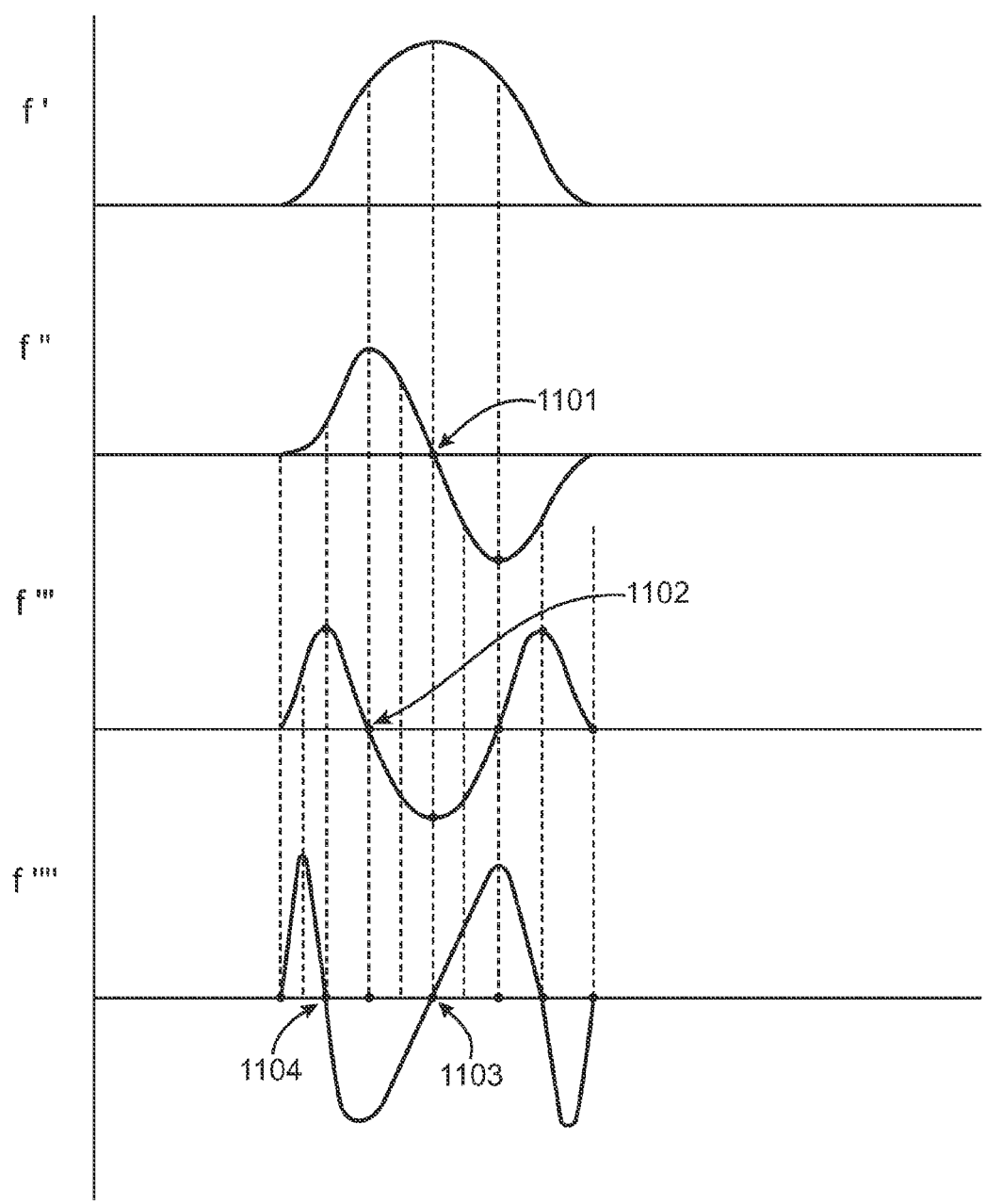
FIG. 11 is an illustration of the calculation of various maximum derivatives of a PCR curve according to one embodiment of the present invention.

FIG. 11 shows an illustration of where the maximum 1st, 2nd, and 3rd derivatives for an amplification curve modeled by a modified sigmoid function is shown. The maximum of a derivative is found at the zero of the next higher order derivative. Zero points 1101 and 1103 are used to find the location of the maximum 1st derivative; zero point 1102 is used to find the location of the maximum 2nd derivative; and zero point 1104 can be used to find the location of the maximum 3rd derivative.

One goal is to find a compromise between the two yielding the best of both cases. This can be accomplished by calculating Ct value as a weighted average of the two derivatives. In one embodiment, the nth and nth+1 derivative values are used in the weighted average. The values of the maximum derivatives can be calculated by using such techniques as iteration or Newton-Raphson algorithms.

The weight parameters used in the weighted average may be adjusted to satisfy a number of criteria. In one embodiment, the weight parameter can be set so that the efficiency of a standard curve is 100% for a known-good, efficiency-weight-parameter calibration file. In this case, a SYBR Green linearity is used as a reference file, but any data file regarded as being of sufficient goodness would suffice. In another embodiment, one may set the weight parameter to minimize sensitivity to variations in the tail of the curve, where amplification may not be faithfully represented by the fluorescence or instrument variability may be an issue.

In some embodiments, the weighted average of the maximum $2^{nd}$ derivative location and the maximum $3^{rd}$ derivative location is used to determine the Ct value, and the weight factor is chosen relative to a SYBR Green Linearity reference file. The formula is as follows:

$Ct$SelectionValue=
  $(1.0-p)$\*Max2ndDerivative$X$Location+
  $p$\*Max3rdDerivative$X$Location.

In one embodiment, the weight value, p, may typically be in the range of 0.3-0.7. For example, one embodiment uses a weight value of 0.65.

If, for some reason, there has been a failure and the weighed averages of the nth and nth+1 derivative cannot be calculated, a Ct value can be determined using another method. For example, the curve can be analyzed within a window. The curve may also be truncated until a result is achieved. If amplification is early, the analysis can be conducted by extrapolating past the beginning If the data shows late amplification, the analysis can be conducted by extrapolating the curve past the end of the curve, and a recalculation can then be attempted.

If all of the above do not yield a valid Ct value, then the system can revert to the approach used in the single threshold method of analysis; see patent applications US2006/0269947 and US2006/0271308. Both of these references are hereby incorporated for all purposes. If none of the above yields a valid Ct value, then less accurate Ct value can be calculated from a lower resolution method.

As discussed above in method 900, once an initial Ct value is determined, e.g., using an average of derivatives, the Ct value can be used to define a region for a higher resolution functional fit. This higher functional fit (e.g., a high order polynomial regression function) can then be used to further refine the Ct value using the average of derivates again. This process, as previously described above, defines a window around the amplification region. By restricting the Ct determination to this amplification window, variability seen at the start and end of the curve can become less relevant to the analysis. As a result, a more accurate Ct value can be determined. The weight value for this case is adjusted to minimize fluctuations due to instrument bias.

When using the Ct value to compare amplification curves, if there are known standards, then a graph known as a standard curve may be created relating the known standard starting quantities to their Ct values. Even if there are no standards, one may use a many-fold dilution set to define a standard curve. A log-linear graph may then be used to project the Ct values for unknown samples to determine their absolute or relative starting quantities depending upon whether absolute standards or multi-fold unknowns are used to define the curve. The slope of this log-linear graph may be used to calculate an efficiency. This efficiency can refer to the average probability that during PCR amplification, the full cycle, consisting of melting, annealing, and extension, results in a doubling of the number of DNA particles. It is generally desirable that this efficiency be less than 1 since there is never perfect doubling at each cycle, but creation of unwanted additional products may give an efficiency greater than 1.

VII. Combined Method

Figure 12:
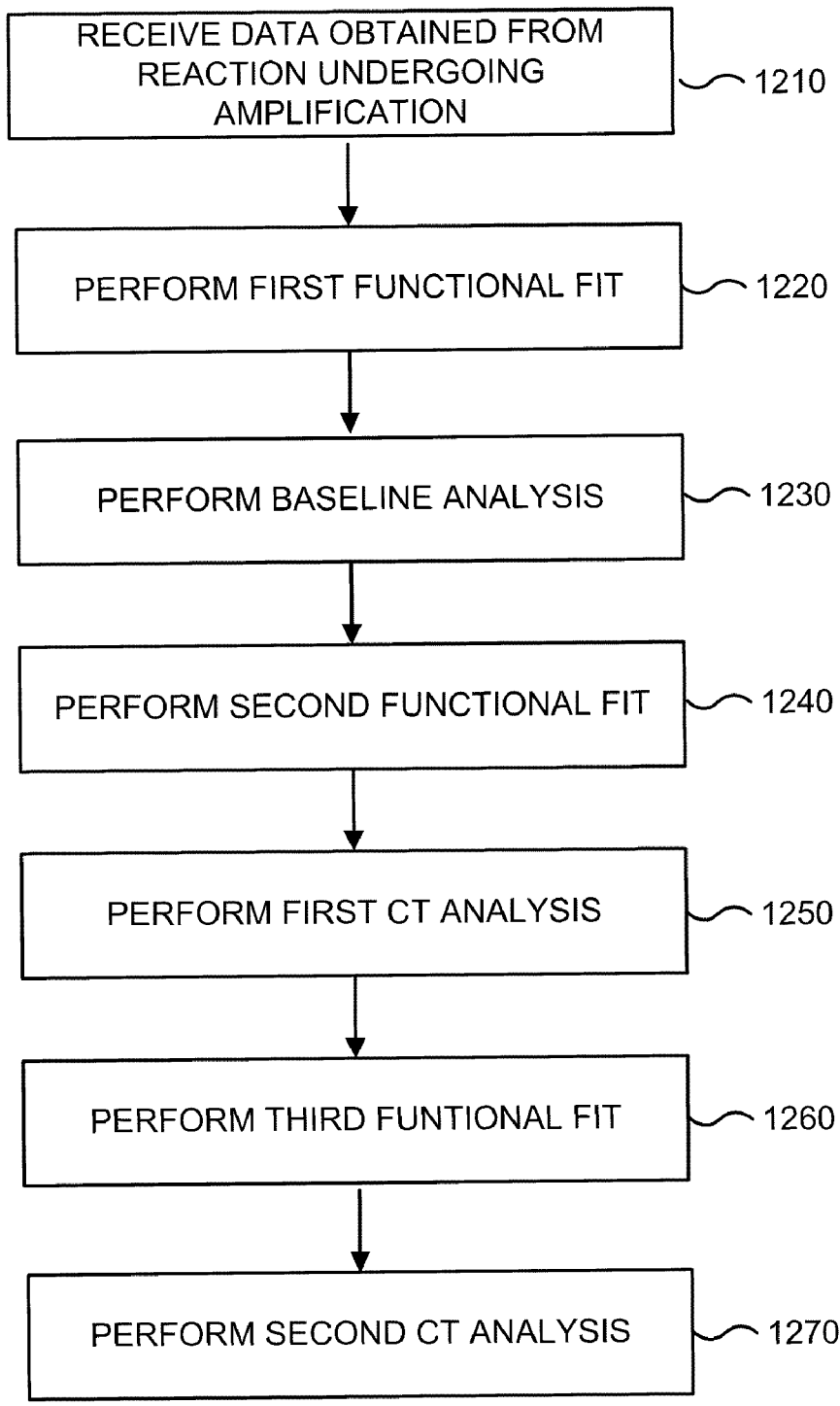
FIG. 12 is a flow diagram illustrating a method of analyzing an amplification curve by performing multiple functional fits to determine a Ct value according to an embodiment of the present invention.

FIG. 12 is a flow diagram illustrating a method of analyzing an amplification curve by performing multiple functional fits to determine a Ct value according to an embodiment of the present invention. Each of the steps in FIG. 12 has been described in much more detail earlier in this disclosure. Many of the steps in FIG. 12 are optional depending on the particular needs of an embodiment. Additionally, many of the various steps outlined in FIG. 12 can be carried out independently of other steps. For example, the baseline analysis shown in FIG. 12 can be conducted independently of any Ct determination.

At step 1210, raw data taken from a biological or chemical reaction undergoing amplification is received for analysis. In some embodiments, the raw data may be color separated. In some embodiments, the raw data may be analyzed to determine whether the data represent amplification. In some embodiments of the invention, the maximum amplification slope bound analysis is conducted to make this determination.

At step 1220, a first functional fit is conducted using the raw data to obtain a first functional approximation of the data. This functional approximation can be used by some embodiments to determine various characteristics of the underlying reaction. In some embodiments, a sigmoid function is used as the first functional approximation.

At step 1230, a baseline analysis is conducted. In some embodiments of the invention, a sigmoid function may be used as a functional approximation of the raw data. In one embodiment, the baseline analysis uses embodiments of method 600.

At step 1240, a second functional fit can be conducted to create a second functional approximation of the data. The first functional approximation may be used to create some of the parameters of the second functional approximation. In some embodiments, the second functional approximation uses a modified sigmoid function, as described above.

At step 1250, the second functional approximation is used to determine a Ct value. In some embodiments, the Ct value is determined using a weighted-average of the cycle numbers where the maximum values of two or more derivatives of the second functional approximation occur. For example, a weighted average of the cycle numbers for the maximum of the $2^{nd}$ derivative and for the maximum of the $3^{rd}$ derivative may be used.

At step 1260, a third functional fit can be conducted to create a third functional approximation of the data. In one embodiment, the Ct value determined at step 1250 is used to define the range of values over which the functional fit of step 1260 operates.

At step 1270, the third functional approximation is used to determine a new Ct value. In some embodiments, this new Ct value is also determined using a weighted-average of the cycle numbers where the maximum values of two or more derivatives of the third functional approximation occur.

The multi stage functional fit as in steps 1220, 1240 and 1260 can be repeated as many times as needed.

VIII. Example System

Figure 13:
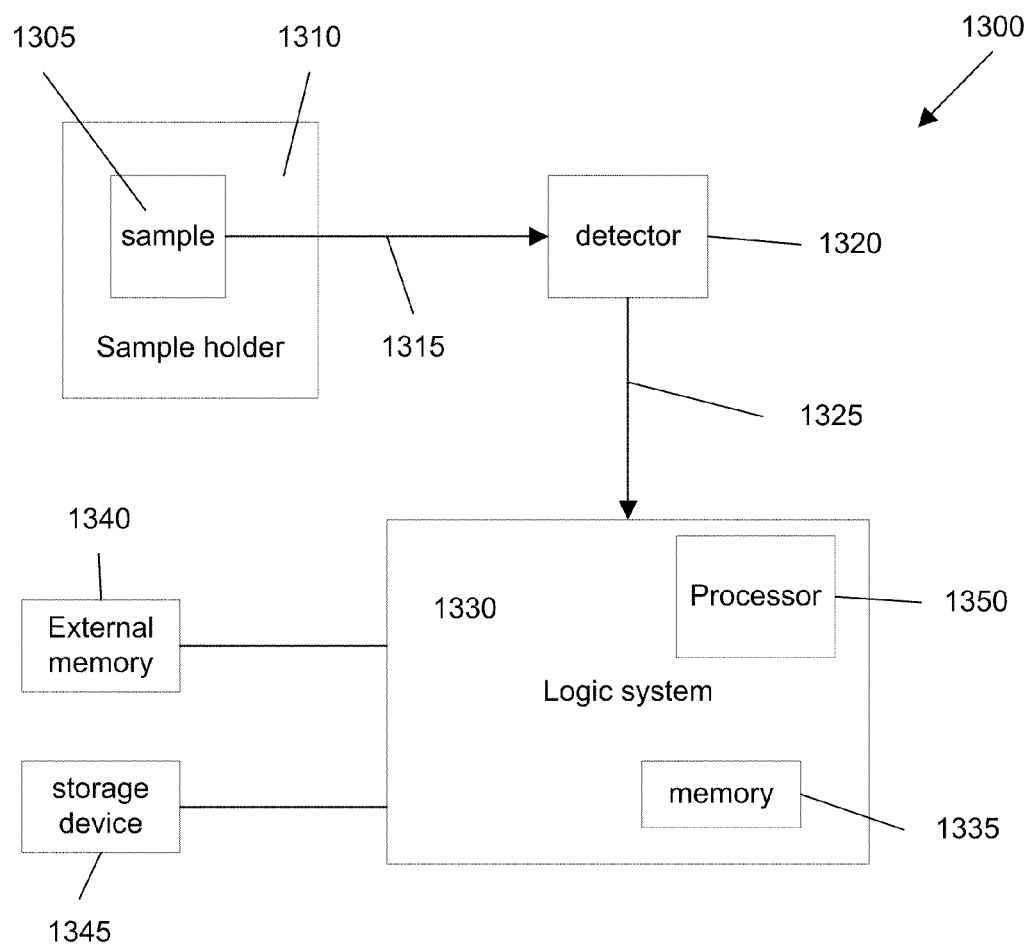
FIG. 13 illustrates a system that processes real-time PCR data according to an embodiment of the present invention.

FIG. 13 illustrates a system 1300 according to one embodiment of the present invention. The system as shown includes a sample 1305, such as bacteria or DNA, within a sample holder 1310. A physical characteristic 1315, such as a fluorescence intensity value, from the sample is detected by detector 1320. A signal 1325, including a noise component, is sent from detector 1320 to logic system 1330. The data from signal 1325 may be stored in a local memory 1335 or an external memory 1340 or storage device 1345. In one embodiment, an analog to digital converter converts an analog signal to digital form.

Logic system 1330 may be, or may include, a computer system, ASIC, microprocessor, etc. It may also include or be coupled with a display (e.g., monitor, LED display, etc.) and a user input device (e.g., mouse, keyboard, buttons, etc.). Logic system 1330 and the other components may be part of a stand alone or network connected computer system, or they may be directly attached to or incorporated in a thermal cycler device. Logic system 1330 may also include optimization software that executes in a processor 1350.

The specific details of the specific aspects of the present invention may be combined in any suitable manner without departing from the spirit and scope of embodiments of the invention. However, other embodiments of the invention may be directed to specific embodiments relating to each individual aspects, or specific combinations of these individual aspects.

It should be understood that the present invention as described above can be implemented in the form of control logic using hardware and/or using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive or an entire computer system), and may be present on or within different computer program products within a system or network. A computer system may include a monitor, printer, or other suitable display for providing any of the results mentioned herein to a user.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

What is claimed is:

1. A method of determining one or more properties of a biological and/or chemical reaction from a data set representing an amplification process of the reaction, the method comprising:
   receiving a set of data points representing a curve having a baseline portion and a growth portion, each data point representing a physical quantity of a substance during an amplification process;
   calculating, with a processor, a first function that approximates the set of data points, wherein calculating the first function includes determining a plurality of parameters that define the first function;
   extracting one or more of the parameters from the first function;
   using the one or more extracted parameters to calculate, with the processor, a second function that approximates the set of data points, the second function having a different functional form than the first function; and
   determining, with the processor, one or more properties of the biological and/or chemical reaction using the second function.

2. The method of claim 1, wherein the one or more properties include a quantitation value associated with the amplification process.

3. The method of claim 1, wherein the one or more parameters are used as initial values for the second function, and wherein calculating the second function includes changing one or more the initial values to reduce an error between the second function and the set of data points.

4. The method of claim 3, wherein the second function is a modified sigmoid function that contains a drift term.

5. The method of claim 4, wherein the modified sigmoid function is represented by:

$$f = a_0 + \frac{1}{D}\left[a_1 + \left(\frac{a_4}{D}\right)\ln\left(\frac{D}{H}\right)\right],$$

where $D=1+h$, $h=\exp(E)$, $$E = \frac{(a_2 - x)}{a_3},$$

where $a_0$, $a_1$, $a_2$, $a_3$, and $a_4$ are parameters determined during a fitting procedure of the modified sigmoid function to the set of data points, and where x is a cycle number of the amplification process.

6. The method of claim 5, wherein the one or more extracted parameters include $a_0$, $a_1$, $a_2$, and $a_3$.

7. The method of claim 1, wherein the one or more properties of the biological and/or chemical reaction include a time Ct in the amplification process at which the second function has a specified value.

8. The method of claim 7, further comprising:
   using the time Ct to calculate a function that approximates a portion of the set of data points by:
   defining a window of time centered at Ct;
   using the data points within the time window to determine the third function such that the third function approximates the data points within the time window.

9. The method of claim 8, wherein the third function is a polynomial of sixth order or higher.

10. The method of claim 7, wherein the time Ct is determined as a weighted average of a first time where a second derivative of the second function has a maximum value and a second time where a third derivative of the second function has a maximum value.

11. The method of claim 1 further comprising:
    selecting an end of the baseline portion as a first time of the amplification process, wherein an integrated area of a first derivative function of the first function from the first time to a peak of the first derivative function is within a range of specified values.

12. The method of claim 1 further comprising:
    analyzing the first function to determine whether a slope of the first function exceeds a maximum amplification slope; and
    if the first function does have locations where the maximum amplification slope is exceeded, then treating segments containing the locations as a non-amplifying segment of the amplification curve.

13. The method of claim 12 wherein the maximum amplification slope is ln(2.0) multiplied by a value of a data point at a location where the slope is being calculated.

14. A method of determining a baseline region for an amplification curve resulting from an amplification process of a biological and/or chemical reaction, the method comprising:
    receiving a set of data points representing a curve having a baseline portion and a growth portion, each data point representing a physical quantity of a substance during an amplification process;
    determining, with a processor, a function that approximates the set of data points;
    calculating a first derivative of the function to obtain a first derivative function;

determining, with the processor, an end of a baseline region by:
for each of a plurality of points:
integrating the first derivative function from the respective point to a fixed location of the first derivative function to obtain a respective integrated area; and
selecting a point whose integrated area is within a specified range as the end of the baseline region; and
determining a beginning of the baseline region.

15. The method of claim 14, wherein the first derivative function includes the first derivative of the function subtracted by the first derivative at an initial data point.

16. The method of claim 15, wherein the integrated area of the selected point is a predetermined percentage of the area the first derivative function from the initial point to the fixed location.

17. The method of claim 14, further comprising:
identifying a peak of the first derivative function, wherein the fixed location on the first derivative function is the peak of the first derivative function.

18. The method of claim 17, wherein the integrating is performed from the peak on the first derivative function toward the beginning of the first derivative function to obtain the respective integrated areas.

19. The method of claim 14, wherein determining the beginning of the baseline region comprises:
determining whether an increase in the value of one data point to a next data point is greater than a predetermined amount; and
if the predetermined amount is exceeded, selecting the beginning of the baseline to be after the one data point.

20. The method of claim 14 wherein determining the beginning of the baseline region comprises truncating one or more data points from the baseline region if the data points of the baseline region do not approximate linear behavior within a threshold value, wherein truncating one or more data points from the baseline region comprises:
i) defining the baseline region as the data points from the beginning of the set data points to the determined end of the baseline region;
ii) analyzing the baseline region to determine whether the baseline region exhibits non-amplifying behavior based on the linear behavior of the data points within the baseline region;
iii) if the baseline region does not approximate linear behavior within the threshold value, removing at least one leading data point from the baseline region;
iv) repeating steps ii-iii until a) the baseline region exhibits non-amplifying behavior, or b) steps ii-iii have been repeated a predefined number of times.

21. A method of determining a reference value of a biological and/or chemical reaction from a data set representing an amplification process of the reaction, the method comprising:
receiving a set of data points representing a curve having a baseline portion and a growth portion, each data point representing a physical quantity of a substance during an amplification process;
determining, with a processor, a function that approximates the set of data points;
calculating, with the processor, at least two different derivatives of the function;
identifying a respective time in the amplification process where each derivative has a maximum value, the respective times for the different derivatives being different;
calculating, with the processor the reference value of the biological and/or chemical reaction as a weighted average of the respective times.

22. The method of claim 21 wherein the at least two derivatives include the second derivative and the third derivative.

23. The method of claim 22, wherein the second derivative is weighted by (1−p) and the third derivative is weighted by p, and wherein p has a value in the range of 0.3-0.7.

24. The method of claim 21, further comprising:
setting the weights for the weighted average such that the efficiency of a reference curve is 100%.

25. A non-transitory computer readable medium storing a plurality of instructions that when executed control a computer system to determine one or more properties of a biological and/or chemical reaction from a data set representing an amplification process of the reaction, the instructions comprising the method of claim 1.

26. A non-transitory computer readable medium storing a plurality of instructions that when executed control a computer system to determine a baseline region for an amplification curve resulting from an amplification process of a biological and/or chemical reaction, the instructions comprising the method of claim 14.

27. A non-transitory computer readable medium storing a plurality of instructions that when executed control a computer system to determine a reference value of a biological and/or chemical reaction from a data set representing an amplification process of the reaction, the instructions comprising the method of claim 21.

* * * * *